US011178506B2

(12) United States Patent
Anders et al.

(10) Patent No.: US 11,178,506 B2
(45) Date of Patent: *Nov. 16, 2021

(54) INTERNET OF THINGS IMPLANTED DEVICE

(71) Applicant: International Business Machines Corporation, Armonk, NY (US)

(72) Inventors: Kelley Anders, East New Market, MD (US); Jeremy R. Fox, Georgetown, TX (US)

(73) Assignee: International Business Machines Corporation, Armonk, NY (US)

( * ) Notice: Subject to any disclaimer, the term of this patent is extended or adjusted under 35 U.S.C. 154(b) by 322 days.

This patent is subject to a terminal disclaimer.

(21) Appl. No.: 15/829,070

(22) Filed: Dec. 1, 2017

(65) Prior Publication Data

US 2019/0174254 A1 Jun. 6, 2019

(51) Int. Cl.
*H04W 4/021* (2018.01)
*G06K 7/10* (2006.01)
*H04L 29/08* (2006.01)
*A61N 1/372* (2006.01)

(52) U.S. Cl.
CPC ............. *H04W 4/021* (2013.01); *A61N 1/372* (2013.01); *G06K 7/10297* (2013.01); *G06K 7/10425* (2013.01); *H04L 67/12* (2013.01)

(58) Field of Classification Search
None
See application file for complete search history.

(56) References Cited

U.S. PATENT DOCUMENTS

| 7,639,006 | B2 | 12/2009 | Deffeyes |
| 8,886,317 | B2 | 11/2014 | Cooke et al. |
| 8,954,030 | B1 | 2/2015 | Buchheit |
| 9,008,788 | B2 | 4/2015 | Jenison |
| 9,630,017 | B1 | 4/2017 | Buchheit |
| 2013/0267826 | A1 | 10/2013 | Sison |
| 2014/0282877 | A1* | 9/2014 | Mahaffey ............ H04L 63/0853 726/3 |

(Continued)

OTHER PUBLICATIONS

List of IBM Patents or Patent Applications Treated as Related, Jan. 31, 2018, 2 pages.

(Continued)

*Primary Examiner* — Jennifer Pitrak McDonald
*Assistant Examiner* — Elizabeth K So
(74) *Attorney, Agent, or Firm* — Heslin Rothenberg Farley & Mesiti P.C.; Scott Dobson, Esq.

(57) ABSTRACT

A method, computer program product, and system includes a processor(s) obtaining a signal from an implanted device within a given vicinity of the one or more processors. The processor(s) identifies a device that when active, has a pre-defined probability of impacting regular functionality of the implanted device. The processor(s) determines coordinates of a perimeter around the device, where the pre-defined probability of the device impacting the regular functionality of the implanted device is realized inside the perimeter. The processor(s) generate a geofence boundary around the device. The processor(s) initiate an action to decrease the pre-defined probability of the device impacting the regular functionality of the implanted device.

5 Claims, 6 Drawing Sheets

(56) References Cited

U.S. PATENT DOCUMENTS

2015/0089590 A1   3/2015   Krishnan et al.

OTHER PUBLICATIONS

Anders et al., "Internet of Things Implanted Device," U.S. Appl. No. 15/855,037, filed Dec. 27, 2017, pp. 1-38.
Mell et al., "The NIST Definition of Cloud Computing", National Institute of Standards and Technology, U.S. Dept. of Commerce, NIST Special Publ. 800-145, Sep. 2011, 7 pages.

\* cited by examiner

INTERNET OF THINGS IMPLANTED DEVICE

BACKGROUND

The Internet of Things (IoT) is a system of interrelated computing devices, mechanical and digital machines, objects, animals and/or people that are provided with unique identifiers and the ability to transfer data over a network, without requiring human-to-human or human-to-computer interaction. These communications are enabled by smart sensors, which include, but are not limited to, both active and passive radio-frequency identification (RFID) tags, which utilize electromagnetic fields to identify automatically and to track tags attached to objects and/or associated with objects and people. Smart sensors, such as RFID tags, can track environmental factors related to an object, including but not limited to, temperature and humidity. The smart sensors can be utilized to measure temperature, humidity, vibrations, motion, light, pressure and/or altitude. IoT devices also include individual activity and fitness trackers, which include (wearable) devices or applications that include smart sensors for monitoring and tracking fitness-related metrics such as distance walked or run, calorie consumption, and in some cases heartbeat and quality of sleep and include smartwatches that are synced to a computer or smartphone for long-term data tracking. Because the smart sensors in IoT devices carry unique identifiers, a computing system that communicates with a given sensor can identify the source of the information. Within the IoT, various devices can communicate with each other and can access data from sources available over various communication networks, including the Internet.

Pacemakers and ICDs (implantable cardioverter defibrillators) are used by individuals globally and enable these individuals to participate in routine activities without concerns that these activities will contribute to an imminent cardiac event. The number of devices in use has increased with the increased age of certain portions of the populations.

For some individuals with routine activities may include travels, which causes the individuals to come into contact with various (security) systems that can have detrimental effects on the operation of these devices, including disrupting the core functionality and draining the battery. The responsibility of detecting these hazards and avoiding them falls to the individual with the device, which is problematic, at least because many individuals who utilize the devices are older and may face challenges related to memory and coherence that are unrelated to the issues beings addressed by the device. Placing the onus on these individuals to follow avoidance protocols is not realistic and does not carry a high likelihood of success. But when avoidance protocols are not followed by individuals, the results can be highly detrimental to the health of the individuals.

SUMMARY

Shortcomings of the prior art are overcome and additional advantages are provided through the provision of a method for maintaining the regular functionality of an implanted device. The method includes, for instance: obtaining, by one or more processors, a signal from an implanted device within a given vicinity of the one or more processors; based on the obtaining, identifying, by the one or more processors, a device, wherein the device, when active, has a pre-defined probability of impacting regular functionality of the implanted device; determining, by the one or more processors, coordinates of a perimeter around the device, wherein the pre-defined probability of the device impacting the regular functionality of the implanted device is realized inside the perimeter; based on determining the perimeter, generating, by the one or more processors, a geofence boundary around the device; and based on generating the geofence, initiating, by the one or more processors, an action to decrease the pre-defined probability of the device impacting the regular functionality of the implanted device.

Shortcomings of the prior art are overcome and additional advantages are provided through the provision of a computer program product for maintaining the regular functionality of an implanted device. The computer program product comprises a storage medium readable by a processing circuit and storing instructions for execution by the processing circuit for performing a method. The method includes, for instance: obtaining, by the one or more processors, a signal from an implanted device within a given vicinity of the one or more processors; based on the obtaining, identifying, by the one or more processors, a device, wherein the device, when active, has a pre-defined probability of impacting regular functionality of the implanted device; determining, by the one or more processors, coordinates of a perimeter around the device, wherein the pre-defined probability of the device impacting the regular functionality of the implanted device is realized inside the perimeter; based on determining the perimeter, generating, by the one or more processors, a geofence boundary around the device; and based on generating the geofence, initiating, by the one or more processors, an action to decrease the pre-defined probability of the device impacting the regular functionality of the implanted device.

Methods and systems relating to one or more aspects are also described and claimed herein. Further, services relating to one or more aspects are also described and may be claimed herein.

Additional features are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1:
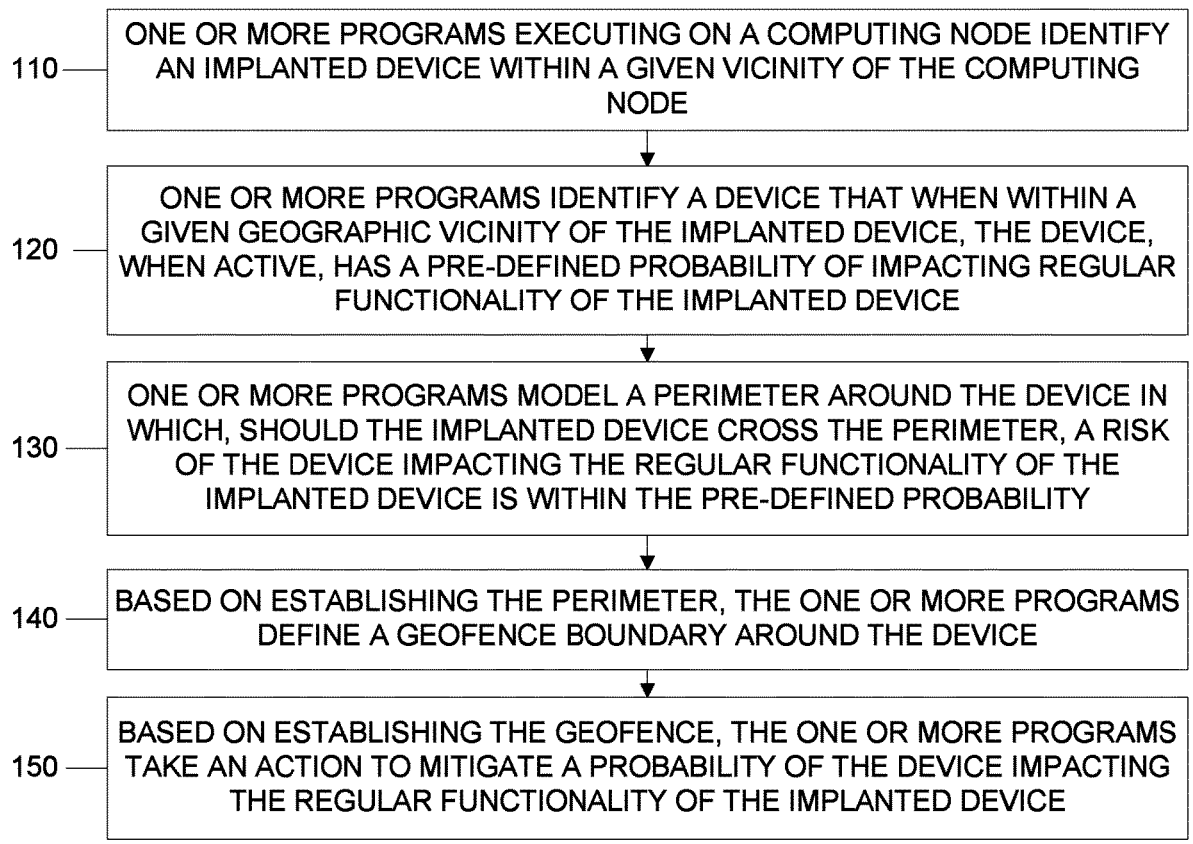
FIG. 1 is a workflow illustrating certain aspects of an embodiment of the present invention.

The accompanying figures, in which like reference numerals may refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

Figure 4:
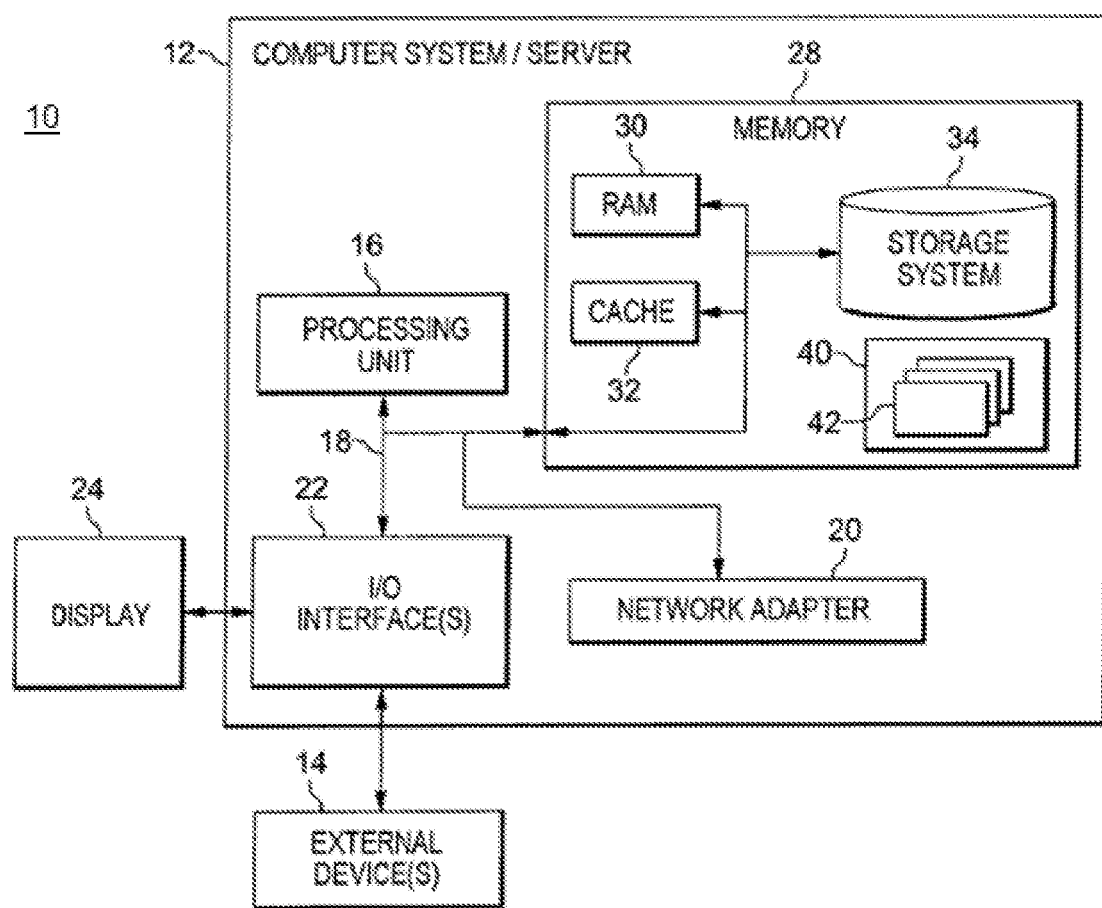
FIG. 4 depicts one embodiment of a computing node that can be utilized in a cloud computing environment.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code. One example of program code, also referred to as one or more programs, is depicted in FIG. 4 as program/utility 40, having a set (at least one) of program modules 42, may be stored in memory 28.

Embodiments of the present invention include a computer-implemented method, a computer program product, and a computer system that include one or more programs for: providing safety measures to protect individuals with individuals with implantable medical devices, such as implantable cardioverter defibrillators (ICDs) and/or pacemakers. These measures may include, but are not limited to, providing alerts both to the individual with the ICD and/or pacemaker, as well as to an entity (system and/or individual) that controls a system that has a potential to negatively impact the functionality of the ICD and/or pacemaker, potentially impacting the health of the individual with the device. Measures may also include temporarily de-activating one or more systems that may impact the functionality of the ICD and/or pacemaker, while the individual with the ICD and/or pacemaker is within a proximity where the system would have this impact. The one or more programs identify systems within a proximity of an individual with an ICD and/or a pacemaker and establish geofences around the systems. A geofence is a virtual geographic boundary for a particular area, defined by global positioning system (GPS) or Radio-frequency identification (RFID) technology, which enables software to trigger a response when a mobile device enters or leaves the particular area.

For purposes of clarity, ICDs and pacemakers are both referred to throughout as implanted devices. An individual characterized as having an implanted device may have one or more ICDs and/or one or more pacemakers.

Embodiments of the present invention are inextricably tied to computing and provide advantages over existing methods of protecting/maintaining the functionality of implanted devices. The utilization of IoT and other computing devices and wireless communications between these devices forms the foundation of certain aspects of some embodiments of the present invention. For example, based on determining the location of both an implanted device and a device that could negatively impact an implanted device, one or more programs can utilize a wireless network to take active measures to maintain the functionality of the implanted device.

Certain embodiments of the present invention include aspects that provide advantages over existing methods of protecting the functionality of implanted devices. Existing methods exist for identifying the presence of implanted devices based on detecting a wireless symbol emanating from the implanted device. However, unlike one or more programs in embodiments of the present invention, these existing methods do not include taking actions to mitigate possible interferences with the routine functionality of the implanted device, including alerting the individual with the implanted device and/or disabling the device that could negatively impact the routine functionality. Embodiments of the present invention can take advantage of existing methods of detecting the presence of implanted devices while providing the added aforementioned enhancements. Some existing systems rely on communications between an implanted device and satellites to regulate the functionality of the pacemaker, should the regular functionality be interrupted. Some embodiments of the present invention represent an improvement over these existing systems because rather than rely on satellite communications to rectify an implanted device's functionality after it has been adversely impacted, embodiments of the present invention mitigate potential issues before they occur.

Additional advantages provided by aspects of some embodiments of the present invention over existing technologies include, but are not limited to: 1) one or more programs that identify the implanted device(s) of an individual and generate proactive notifications to multiple (e.g., designated) parties based on determining that there is a risk within a proximity of the implanted device; 2) one or more programs that identify the safety measures associated with a previously identified implanted device, monitor environmental factors, and generate notifications or preventative actions when the environmental factors present a risk to the implanted device; 3) one or more programs that quantify risks posed by an implanted device being within a pre-defined vicinity of a given device and provide the quantified risk to one more parties in a visually comprehensive manner, in a GUI (e.g., green indicates the current location is safe, yellow indicates a warning for the current location, and red indicates an alert); 4) one or more programs that generate geofences and share coordinates for the geofences with other users, in a multi-user computing environment (i.e., a cloud computing environment); 5) one or more programs that are hardware elements that provide notifications when the implanted device approaches or crosses a geofence; and/or 6) one or more programs that configure a connection between an implanted device and a personal computing device and broadcast a location of the implanted device and commands for preventative actions, via the personal computing device, to conserve power within the implanted device.

FIG. 1 is a workflow 100 that illustrates certain aspects of some embodiments of the present invention. Per FIG. 1, in some embodiments of the present invention, one or more programs executing on one or more processors of a computing node identify an implanted device within a given vicinity of the computing node (110). The computing node may be a mobile device and/or an IoT device. This computing node may be paired with the implanted device via a wireless connection, including but not limited to, Bluetooth. The vicinity may be a predetermined area and/or an area calculated by the one or more programs based on attributes of the identified implanted device.

The one or more programs identify a device that when within a given geographic vicinity of the implanted device, the device, when active, has a pre-defined probability of impacting regular functionality of the implanted device (120). In some embodiments of the present invention, the one or more programs may scan a given area for the presence of an IoT or other computing device that is associated with or internal to the problematic device. In some embodiments of the present invention, the one or more programs may communicate directly with the device to determine its presence. Depending upon the communication capabilities of the device, the one or more programs may obtain responses from the device based on pinging the device or the device may broadcast its presence automatically and the one or more programs may include a listener that continuously collects data related to the present of such devices. In some embodiments of the present invention, the geographic vicinity may be preconfigured based upon the type of implanted device. The one or more programs may search a vicinity that is greater than any contemplated geofence, such that the one or more programs may perceive a hazard because the hazard can compromise the functionality of an implanted device.

Based on identifying the device, the one or more programs model a perimeter around the device in which, should the implanted device cross the perimeter, a risk of the device impacting the regular functionality of the implanted device is within the pre-defined probability (130). Based on establishing the perimeter, the one or more programs define a geofence boundary around the device (e.g., utilizing GPS or RFID) (140).

Based on establishing the geofence, the one or more programs take an action to mitigate a probability of the device impacting the regular functionality of the implanted device (150). The actions may include, but are not limited to, one or more of issuing an alert to the device based on determining that the implanted device is within a pre-defined distance of the geofence (including having come into contact with or crossed a boundary of the geofence, and/or within an area bounded by the geofence), temporarily disabling the device while the implanted device is within a pre-defined distance of the geofence and/or within the geofence, issuing a request to the device to disable while the implanted device is within a pre-defined distance of the geofence and/or within the geofence, and/or issuing an alert on an IoT device within a vicinity of the implanted device (e.g., a watch, fitness tracker, phone, etc., carried by or worn by the person with the implanted device).

In some embodiments of the present invention, the one or more programs model a perimeter around the device, based on identifying one or more of: 1) the type of implanted device; and 2) the type of device. Certain types of implanted devices may be most effective outside of a certain perimeter of devices that could impact their regular functionality. Additionally, certain devices may have a known high probability of being problematic for most implanted devices, based on the implanted devices being within a certain proximity of the devices. Thus, the one or more programs may identify one or more of the implanted device and the device in order to set the perimeter.

In some embodiments of the present invention, the one or more programs may provide an individual with an implanted device with a visual alert before the individual is within a problematic distance of the perimeter of a device. For example, in some embodiments of the present invention, the one or more programs may generate a graphical user interface (GUI) or the computing node (e.g., personal computer device of the individual) and provide a graphical representation, such as a map, of the perimeter, the device, and the position of the implanted device. The one or more programs may utilize a location device within the computing node to provide the initial visual and to update this visual as the user moves.

Figure 2:
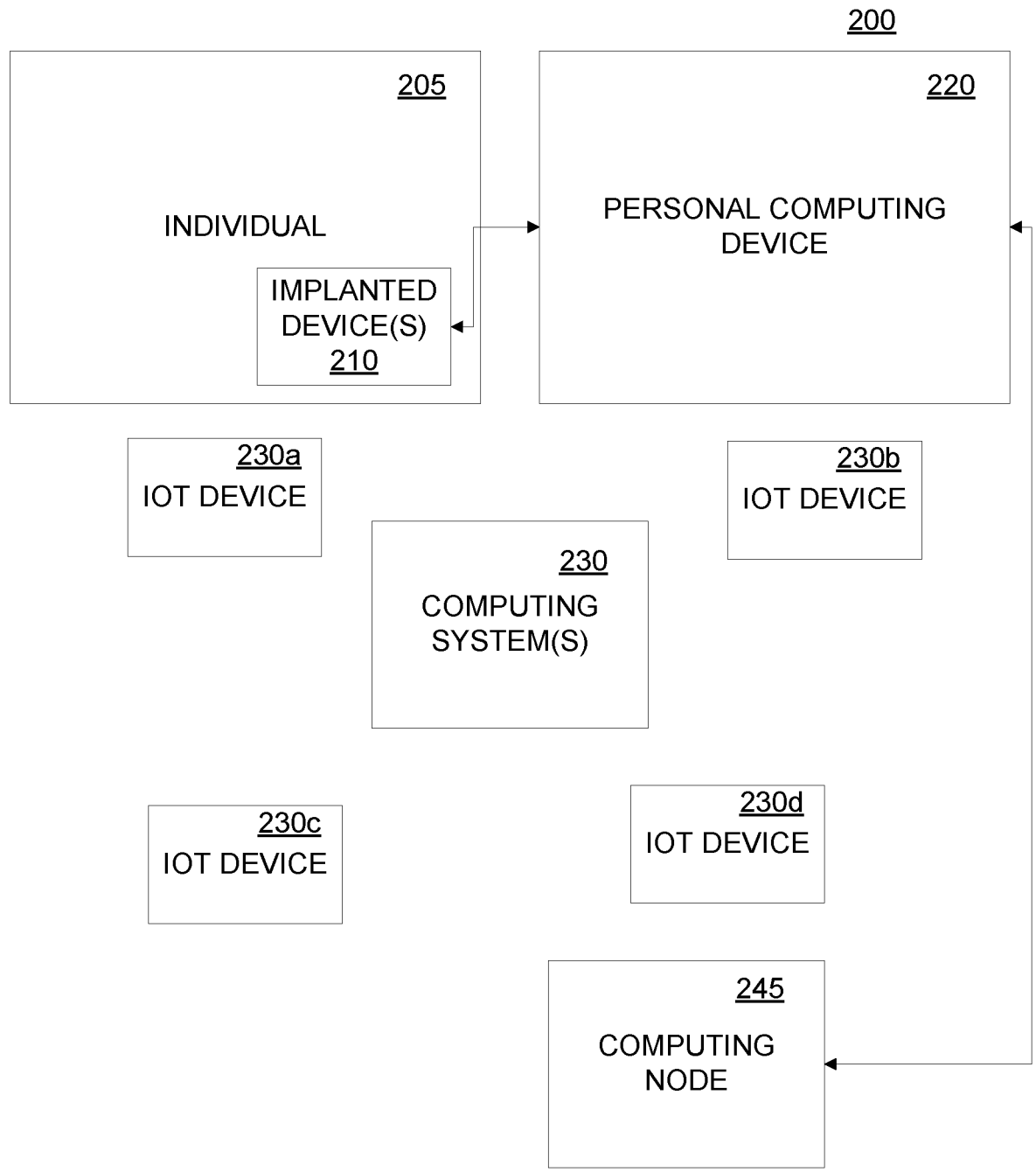
FIG. 2 is an illustration of certain aspects of a technical environment into which certain aspects of an embodiment of the present invention may be implemented.

FIG. 2 is a technical computing environment 200 into which certain aspects of embodiments of the present invention can be implemented. As understood by one of skill in the art, the use of this technical computing environment 200 is merely exemplary and does not impose any limitations on embodiments of the present invention.

Referring to FIG. 2, the technical environment 200 includes an individual 205 with one or more implanted devices 210 within his or her physical body. Proximate to the individual 205, is at least one personal computing device 220 (e.g., an IoT device, a smartphone, a fitness tracker, etc.). The technical environment 200 also includes one or more systems 230 that would affect the functionality of at least one of the one or more implanted devices 210, when the one or more implanted devices 210 are within a given vicinity of the one or more systems 230. Within some geographic proximity of the one or more systems 230, are IoT devices 240*a*-240*d*, which may include RFID tags, sensors, etc. The personal computing device 220 is in communication with a computing node 245 of a shared computing environment over a wireless connection, including but not limited to, the Internet. The computing node 245 may comprise one or more resources of a cloud computing system. Aspects of some embodiments of the present invention are discussed utilizing this technical computing environment 200 to illustrate certain functionality.

In some embodiments of the present invention, one or more programs executed on one or more processors of the personal computing device 220 establish a communication channel with the implanted devices 210. In some embodiments of the present invention, the one or more programs may monitor the signal from the implanted device and provide an alert via the personal computing device 220, when the one or more programs detect irregularities in the signal from the implanted device 210.

The one or more programs executing on the personal computing device 220 identify one or more systems 230 within a pre-defined vicinity of the implanted device 210 that could impact regular functionality of the implanted device 210. In some embodiments of the present invention, the one or more programs identify the one or more systems 230 by broadcasting a message, either continuously or when alerted (e.g., through the individual's 205 input) that the individual 205 is entering an area where one or more systems 230 are likely to be situated. For example, one or more systems 230 that interfere with the functionality of an implanted device are more likely to be located in an airport, train stations, subway station, sports stadium, court house and/or hospital. An IoT device 240*a*-240*d* may also provide an alert to the one or more programs of the personal computing device 220. For example, the one or more programs may broadcast the presence of the implanted devices 210 and an IoT device 240*a*-240*d* may respond that there are one or more systems 230 nearby that could affect the implanted device 210. The IoT device 240*a*-240*d* may also continuously broadcast this information and the one or more programs may obtain the broadcasted data.

Based on identifying one or more systems 230 within a pre-defined vicinity of the implanted device 210 that could impact regular functionality of the implanted device 210, the one or more programs establish a geofence around each of the one or more systems 230. The geofence may be circular and may be established by the one or more programs identifying one or more IoT devices 240*a*-240*d* proximate to boundaries of the geofence, such that a portion of the IoT devices 240*a*-240*d* form the geofence. In some embodiments of the present invention, should an individual with an implanted device cross a geofence boundary, the individual will receive an alert (e.g., on his or her personal computing device, which is paired with his or her implanted device, which the one or more IoT devices 240*a*-240*d* detected), from one or more of the one or more IoT devices 240*a*-240*d*.

In some embodiments of the present invention, the one or more programs define different areas bounded by the geofence, based on the severity of the anticipated effects of the one or more systems 230 on the implanted device 210, within these areas.

Figure 3:
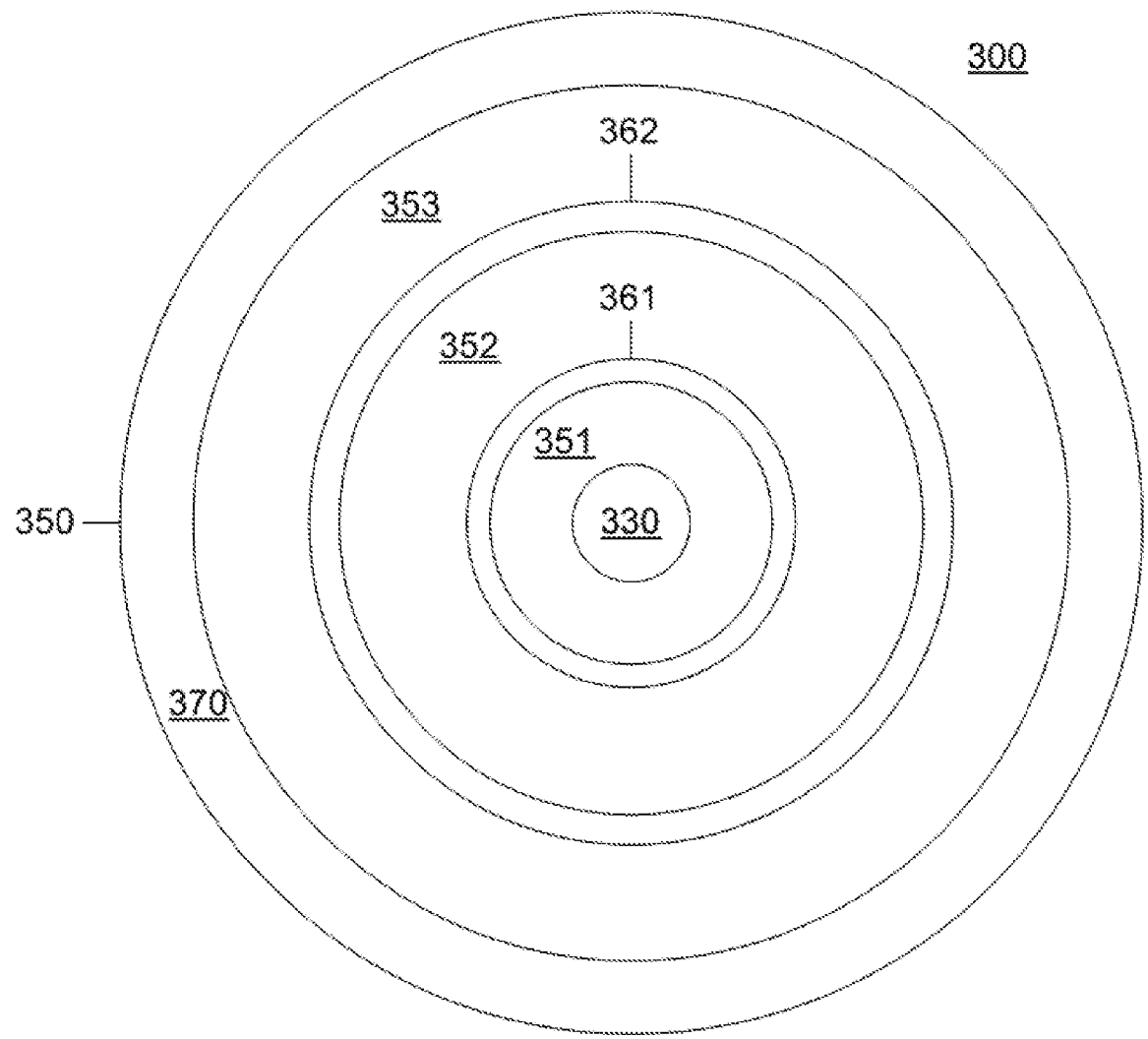
FIG. 3 is an illustration of certain aspects of an embodiment of the present invention.

FIG. 3 provides a visual representation of an area 350, bounded by a geofence 370, with a system 330 that could impact the functionality of an implanted device, located at the center of the area 350. The one or more programs defined sub-areas 351 352 353, within the area 350. A first area 351, which is terminates ata perimeter 361, is closest to the system 330. A second area 352, located outside of the perimeter 361 of the first area and bounded by a second perimeter 362, is further from the system 330. A third area 353 is located between the geofence 370 boundary and the second smallest perimeter 362. In some embodiments of the present invention, to define a geofence 370 and (optionally) any areas with the boundaries of the geofence 370, the one or more programs utilize identifying information about the implanted device (e.g., FIG. 2 210) and/or the system 330 predicted to affect the functionality of the implanted device (e.g., FIG. 2 210).

In some embodiments of the present invention, upon identifying an implanted device (e.g., FIG. 2 210), the one or more programs establish a safe distance from this implanted device for any system 330. The one or more programs may utilize this safe distance when setting the boundaries of the geofence 370 and defining safety levels for sub-areas bounded by the geofence 370. Alternatively, upon identifying a system 330, the one or more programs establish a safe distance from this system 330 for an implanted device (e.g., FIG. 2 210). The one or more programs may utilize this safe distance when setting the boundaries of the geofence 370 and defining safety levels for sub-areas bounded by the geofence 370. The one or more programs may also utilize a combination of attributes of the implanted device (e.g., FIG. 2 210) and the system 330 to set the boundaries of each geofence 370.

As illustrated in FIG. 1, the one or more programs (e.g., executed by a personal computing device 220) take an action to mitigate a probability of the device (e.g., FIG. 2, one or more systems 230) impacting the regular functionality of the implanted device (e.g., FIG. 2, 210) (150). In some embodiments of the present invention, the action taken by the one or more programs to mitigate risk to the device (e.g., FIG. 2, 210) may depend on the location of an individual (e.g., FIG. 2, 205) with the implanted device (e.g., FIG. 2, 210) within a geofenced area around the device (e.g., FIG. 2, one or more systems 230). Referring to FIG. 4, when an individual (e.g., FIG. 2, 205) is located in the third area 353, the one or more programs may either provide no alert or may generate a GUI that indicates a "safe" status (e.g., a green color). When this individual enters the second area 352, the one or more programs may provide a warning to the individual via the personal computing device, such as generating a GUI that indicates a "warning" status (e.g., a yellow color). Should the individual enter the first area 351, the one or more programs may provide an emergency alert to the individual, via the personal computing device, such as generating a GUI that indicates a "warning" status (e.g., a red color). In addition to issuing the alert on the personal computing device, the one or more programs may broadcast the alert to IoTs and other devices within a given vicinity of the individual. Thus, other individuals may be able to assist the individual in exiting the potentially hazardous area.

Returning to FIG. 2, alerting one or more parties of a potential hazard is one of many actions the one or more programs executing on the personal computing device 220 may take to mitigate a probability of the device impacting the regular functionality of the implanted device (e.g., FIG. 1, 150). In addition to, or instead of, issuing an alert, the one or more programs may suspend operations of the one or more systems 230 when the individual 205 (as located utilizing the personal computing device 220 or other IoT device) is within an area that would trigger an alert. For example, a wand utilized at an airport is a system that could negatively impact the functionality of an implanted device 210. The one or more programs may suspend the functionality of the wand while the individual 205 is within a certain vicinity of the wand. The one or more programs may also issue notifications to an administrator of a system that will impact an individual with an implanted device.

Referring to FIG. 2, in some embodiments of the present invention, a portion of the one or more programs illustrated in FIG. 1 may be executed by one or more processor of the computing node 245. For example, in some embodiments of the present invention, the one or more programs may receive a notification from the personal computing device 220 of the location of the implanted device 210. Responsive to this notification, the one or more programs on the computing node 245 may scan a vicinity proximate to the implanted device 210 for systems 230 that could impact the functionality of the implanted device 210. Upon locating a system, in some embodiments of the present invention: 1) the one or more programs alert the personal computing device 220 to the system and the personal computing device 220 establishes a geofence (e.g., FIG. 3, 370); 2) the one or more programs executed on the computing node 245 establish a geofence (e.g., FIG. 3, 370) and communicate the boundaries to the personal computing device, which utilizes the boundaries of the geofence (e.g., FIG. 3, 370) to initiate actions to protect the functionality of the implanted device 210; and/or 3) the one or more programs executed on the computing node 245 establish a geofence (e.g., FIG. 3, 370) and initiate actions to protect the functionality of the implanted device 210, including triggering alerts in the personal computing device 220. In some embodiments of the present invention, the personal computing device 220 establishes a geofence (e.g., FIG. 3, 370) and communicates the boundaries to the computing node 245. The computing node 245 shares this data with other devices in communication with the computing node 245. The computing node 245 may also communicate geofences generated by the other devices to the personal computing device 220.

Some embodiments of the present invention include a computer-implemented method, a computer program product, and a computer system that includes one or more programs executed by one or more processors that obtain a signal from an implanted device within a given vicinity of the one or more processors. Based on the obtaining, the one or more programs identify a device, where the device, when active, has a pre-defined probability of impacting regular functionality of the implanted device. The one or more programs determine coordinates of a perimeter around the device, where the pre-defined probability of the device impacting the regular functionality of the implanted device is realized inside the perimeter. Based on determining the perimeter, the one or more programs generate a geofence boundary around the device. Based on generating the geofence, the one or more programs initiate an action to decrease the pre-defined probability of the device impacting the regular functionality of the implanted device. In some embodiments of the present invention, the implanted device is an implantable cardioverter defibrillator or a pacemaker.

In some embodiments of the present invention, the one or more programs initiate an action by detecting that the implanted device is within a pre-defined vicinity of the device and displaying an alert in a graphical user interface of a computing node comprising the one or more processors.

In some embodiments of the present invention, the one or more programs define one or more areas within the geofence boundary. The one or more programs determine a risk level for each area of one or more areas within the geofence boundary, where the risk level for each of the one or more areas represents a likelihood of experiencing the pre-defined probability of the device impacting the regular functionality of the implanted device, when the implanted device is located within the area. In these embodiments, the one or more programs may initiate the action by detecting that the implanted device is within a first area of the one or more areas. The one or more programs configure a communication, based on a risk level of the first area. The one or more programs display an alert on a graphical user interface of a computing node comprising the one or more processors, based on the risk level of the first area.

In some embodiments of the present invention, the geofence boundary is a circle around the device, where every point of the geofence boundary is equidistant from the device.

In some embodiments of the present invention, the one or more programs initiate the action by detecting that the implanted device has crossed a point on the geofence boundary. The one or more programs temporarily disable the device. The one or more programs re-enable the device, based on detecting that the implanted device is no longer at a location in an area bounded by the geofence.

In some embodiments of the present invention, the one or more programs identify an Internet of Things device closer to the geofence boundary than the implanted device. The one or more programs command the Internet of Things device to issue a warning if the implanted device crosses the perimeter.

In some embodiments of the present invention, the one or more programs initiate an action by identifying one or more Internet of Things devices within the given vicinity. The one or more programs detect that the implanted device has crossed a point on the geofence boundary. The one or more programs transmit an alert to the one or more Internet of Things devices.

In some embodiments of the present invention, the one or more programs identify one or more attributes of the implanted device. In these embodiments, the one or more programs determine the coordinates by utilizing the one or more attributes to determine a safe distance of the implanted device from the device.

In some embodiments of the present invention, the one or more programs transmit a location of the geofence to a shared computing resource.

In some embodiments of the present invention, the one or more programs query the shared computer resource for locations of one or more geofences. The one or more programs obtain a location of an additional geofence. Based on obtaining the location of the additional geofence, the one or more programs initiate an action to decrease a pre-defined probability of an additional device within a boundary of the additional geofence from impacting the regular functionality of the implanted device.

In some embodiments of the invention, a personal computing device includes the one or more processors and the one or more programs obtain the signal by pairing the personal computing device with the implanted device to establish a communication channel. The one or more programs obtain the signal from the implanted device over the communication channel.

In some embodiments of the present invention, the one or more programs initiate the action by broadcasting a message indicating presence of the implanted device, where based on a computing node receiving the message when the implanted device is beyond the geofence boundary, the computing node disables the device.

Referring now to FIG. 4, a schematic of an example of a computing node, which can be a cloud computing node 10. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove. In an embodiment of the present invention, the computing resources including the personal computing device 230 (FIG. 2), the one or more systems 230 (FIG. 2), and the computing node 245 (FIG. 2) can be understood as one or more cloud computing nodes 10 (FIG. 4) and if not examples of a cloud computing node 10, then one or more general computing nodes that include aspects of the cloud computing node 10.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 that can be utilized as cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
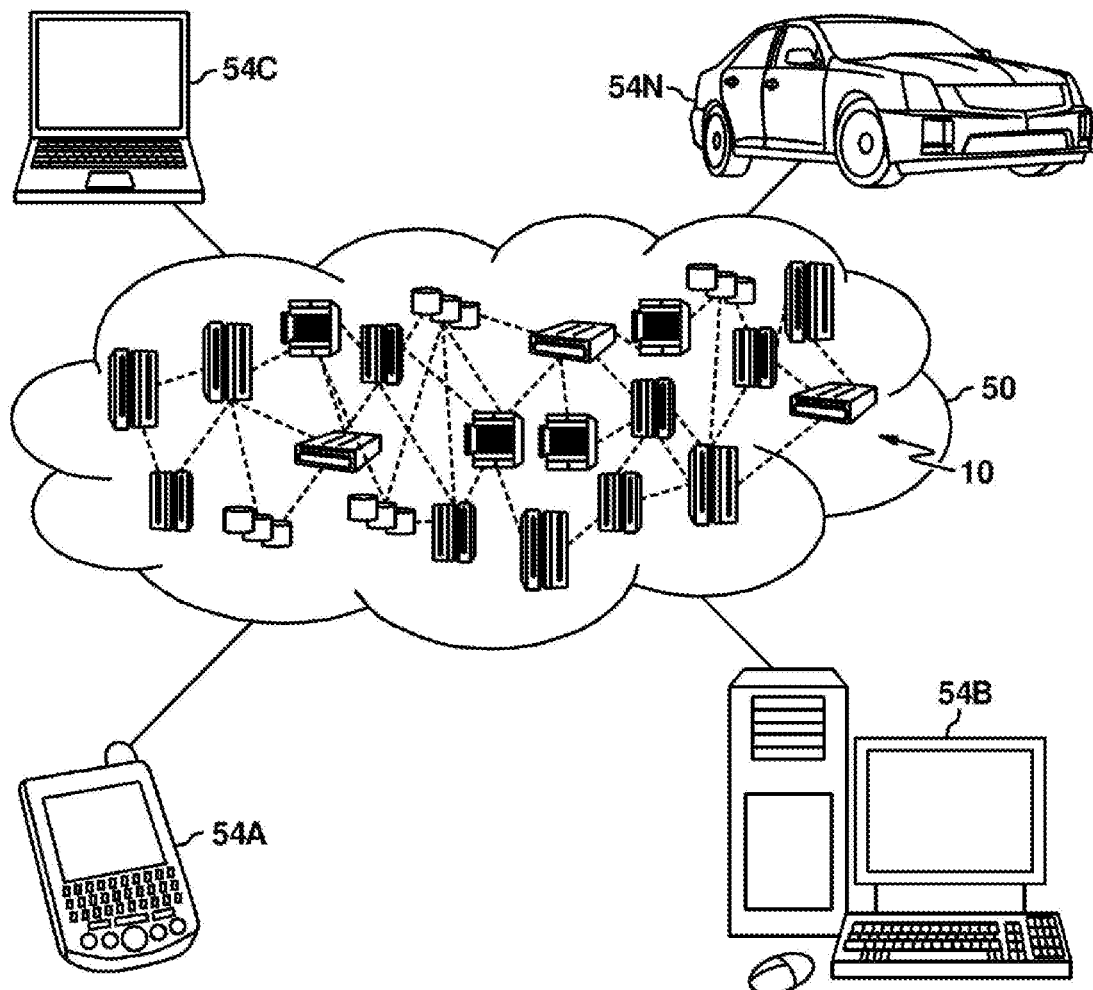
FIG. 5 depicts a cloud computing environment according to an embodiment of the present invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
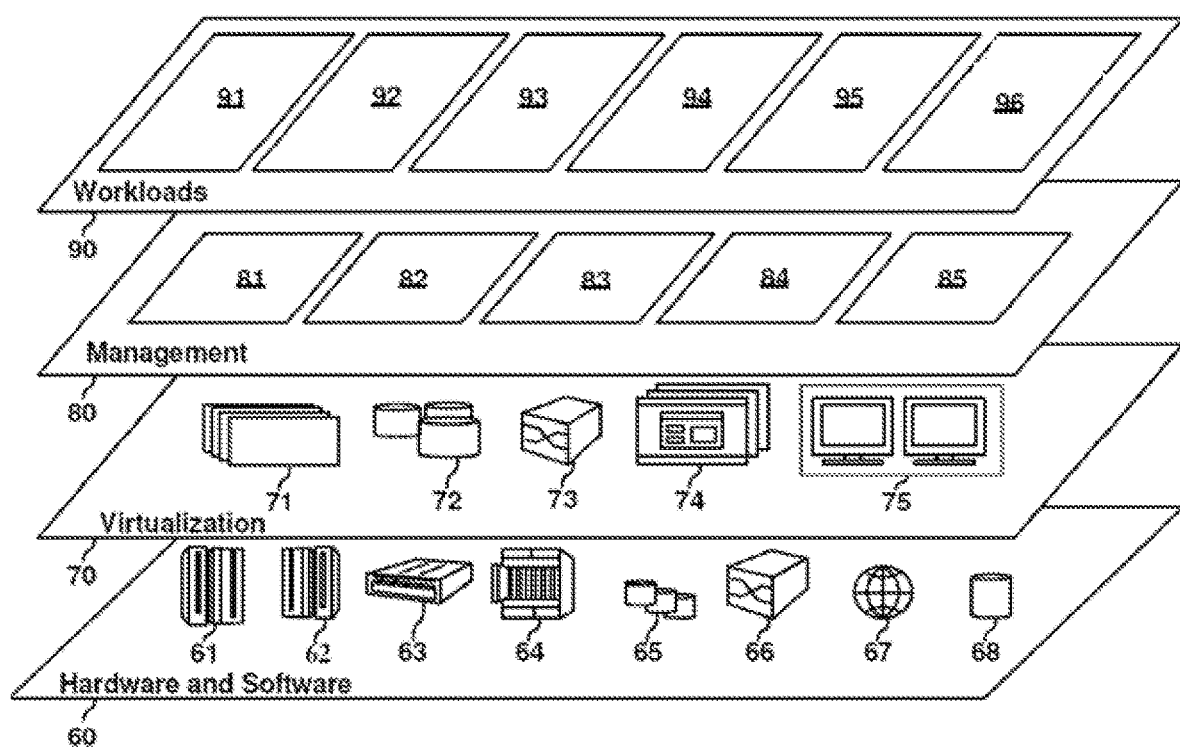
FIG. 6 depicts abstraction model layers according to an embodiment of the present invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and interacting establishing geofences around various systems 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer program product comprising:
   a non-transitory computer readable storage medium readable by one or more processors and storing instructions for execution by the one or more processors for performing a method comprising:
   obtaining, by the one or more processors, a signal from an implanted device within a given vicinity of the one or more processors;
   based on the obtaining, identifying, by the one or more processors, a device, wherein the device, when active, executes a process that has a pre-defined probability of adversely impacting regular functionality of the implanted device, wherein the adversely impacting comprises impairing the regular functionality of the implanted device;
   based on attributes of the implanted device and on attributes of the process, determining, by the one or more processors, coordinates of at least two perimeters around the device, wherein the at least two perimeters comprise a first perimeter and a second perimeter, wherein a first area bounded by the first perimeter comprises a second area bounded by the second perimeter, and wherein the first perimeter is larger than the second perimeter, and wherein the second area is closest to the device of any area bounded by a perimeter of the at least two perimeters;

based on determining the at least two perimeters, generating, by the one or more processors, a geofence, wherein the geofence comprises a geofence boundary around the device at each perimeter of the at least two perimeters;

determining, by the one or more processors, a risk level for each area bounded by the at least two perimeters, wherein the risk level for each of the one or more areas represents a likelihood of experiencing the pre-defined probability of the process executed by the device impacting the regular functionality of the implanted device, when the implanted device is located within the area, wherein the pre-defined probability of the process executed by the device adversely impacting the regular functionality of the implanted device is realized inside the second area;

automatically assigning, by the one or more processors, at least one action of one or more predefined actions to each area bounded by the at least two perimeters, wherein each assigned action of the one or more predefined actions, when initiated by the one or more processors, decreases the pre-defined probability of the process executed by the device impacting the regular functionality of the implanted device, wherein the one or more predefined actions do not impact the regular functionality of the implanted device, and wherein each assigned action is based on a location of the implanted device in an area of the one or more areas;

based on generating the geofence, initiating, by the one or more processors, at least one assigned action, wherein initiating the at least one assigned action comprises:
 detecting, by the one or more processors, that the implanted device has crossed a point on at least one geofence boundary of the geofence;
 determining, by the one or more processors, the location of the point on the at least one geofence boundary;
 based on determining that the location of the point on the at least one geofence boundary is within the second area, temporarily disabling, by the one or more processors, the process executed by the device, wherein the temporarily disabling suspends a functionality of the device;
 issuing, by the one or more processors, a notification to an administrator of the device that the device will impact the regular functionality of the implanted device, wherein the notification includes a location of the implanted device; and
 based on having temporarily disabled the process, re-enabling, by the one or more processors, the process executed by the device, based on detecting that the implanted device is no longer at a location in an area bounded by the geofence.

2. The computer program product of claim 1, wherein the implanted device is selected from the group consisting of: an implantable cardioverter defibrillator and a pacemaker.

3. The computer program product of claim 1, wherein initiating, the at least one assigned action comprises:
 detecting, by the one or more processors, that the implanted device is within the first area;
 configuring, by the one or more processors, a communication, based on a risk level of the first area; and
 displaying, by the one or more processors, an alert on a graphical user interface of a computing node comprising the one or more processors, based on the risk level of the first area.

4. The computer program product of claim 1, wherein each geofence boundary around the device at each perimeter of the at least two perimeters comprising geofence boundaries comprises a circle around the device, wherein every point of each geofence boundary is equidistant from the device, and wherein the geofence boundaries comprise concentric circles.

5. A system comprising:
 a memory;
 one or more processors in communication with the memory;
 program instructions executable by the one or more processors via the memory to perform a method, the method comprising:
  obtaining, by the one or more processors, a signal from an implanted device within a given vicinity of the one or more processors;
  based on the obtaining, identifying, by the one or more processors, a device, wherein the device, when active, executes a process that has a pre-defined probability of adversely impacting regular functionality of the implanted device, wherein the adversely impacting comprises impairing the regular functionality of the implanted device;
  based on attributes of the implanted device and on attributes of the process, determining, by the one or more processors, coordinates of at least two perimeters around the device, wherein the at least two perimeters comprise a first perimeter and a second perimeter, wherein a first area bounded by the first perimeter comprises a second area bounded by the second perimeter, and wherein the first perimeter is larger than the second perimeter, and wherein the second area is closest to the device of any area bounded by a perimeter of the at least two perimeters;
  based on determining the at least two perimeters, generating, by the one or more processors, a geofence, wherein the geofence comprises a geofence boundary around the device at each perimeter of the at least two perimeters;
  determining, by the one or more processors, a risk level for each area bounded by the at least two perimeters, wherein the risk level for each of the one or more areas represents a likelihood of experiencing the pre-defined probability of the process executed by the device impacting the regular functionality of the implanted device, when the implanted device is located within the area, wherein the pre-defined probability of the process executed by the device adversely impacting the regular functionality of the implanted device is realized inside the second area;
  automatically assigning, by the one or more processors, at least one action of one or more predefined actions to each area bounded by the at least two perimeters, wherein each assigned action of the one or more predefined actions, when initiated by the one or more processors, decreases the pre-defined probability of the process executed by the device impacting the regular functionality of the implanted device, wherein the one or more predefined actions do not impact the regular functionality of the implanted device, and wherein each assigned action is based on a location of the implanted device in an area of the one or more areas;

based on generating the geofence, initiating, by the one or more processors, at least one assigned action, wherein initiating the at least one assigned action comprises:

detecting, by the one or more processors, that the implanted device has crossed a point on at least one geofence boundary of the geofence;

determining, by the one or more processors, the location of the point on the at least one geofence boundary;

based on determining that the location of the point on the at least one geofence boundary is within the second area, temporarily disabling, by the one or more processors, the process executed by the device, wherein the temporarily disabling suspends a functionality of the device;

issuing, by the one or more processors, a notification to an administrator of the device that the device will impact the regular functionality of the implanted device, wherein the notification includes a location of the implanted device; and based on having temporarily disabled the process, re-enabling, by the one or more processors, the process executed by the device, based on detecting that the implanted device is no longer at a location in an area bounded by the geofence.

\* \* \* \* \*